United States Patent
Ettlinger et al.

[11] Patent Number: 6,022,404
[45] Date of Patent: *Feb. 8, 2000

[54] SURFACE-MODIFIED, PYROGENICALLY PRODUCED MIXED OXIDES, METHOD OF THEIR PRODUCTION AND USE

[75] Inventors: Manfred Ettlinger, Karlstein; Werner Hartmann, Babenhausen; Dieter Kerner, Hanau; Jürgen Meyer, Rheinfelden, all of Germany

[73] Assignee: Degussa Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/585,313

[22] Filed: Jan. 11, 1996

[30] Foreign Application Priority Data

Jan. 12, 1995 [DE] Germany .................. 195 00 674

[51] Int. Cl.[7] .............. C09C 1/62; C09C 1/36; C09C 1/22

[52] U.S. Cl. .............. 106/404; 106/287.17; 106/287.34; 106/287.11; 106/287.14; 106/287.15; 106/287.16; 106/437; 106/438; 106/439; 106/441; 106/442; 106/445; 106/446; 106/447; 106/448; 106/450; 106/451; 106/456; 106/457; 106/459; 106/460; 106/479; 106/482; 106/483; 106/490

[58] Field of Search .............. 106/310, 287.17, 106/287.27, 287.28, 287.34, 437, 438, 439, 441, 442, 445, 446, 447, 448, 450, 451, 456, 457, 459, 460, 479, 482, 483, 490, 287.11, 287.14, 287.15, 287.16, 404

[56] References Cited

U.S. PATENT DOCUMENTS

| | | | |
|---|---|---|---|
| 3,024,126 | 3/1962 | Brown | 106/310 |
| 3,873,337 | 3/1975 | Läufer et al. | 106/481 |
| 3,920,865 | 11/1975 | Läufer et al. | 427/220 |
| 4,007,050 | 2/1977 | Läufer et al. | 106/483 |
| 4,022,152 | 5/1977 | Läufer et al. | 118/716 |
| 4,902,570 | 2/1990 | Heinemann et al. | 428/405 |
| 5,002,918 | 3/1991 | Deller et al. | 502/263 |
| 5,035,748 | 7/1991 | Burow et al. | 106/499 |
| 5,153,030 | 10/1992 | Chatfield et al. | 427/221 |
| 5,429,873 | 7/1995 | Deusser et al. | 106/287.27 |

FOREIGN PATENT DOCUMENTS

| | | |
|---|---|---|
| 0 212 870 A2 | 3/1987 | European Pat. Off. . |
| 0 373 426 | 6/1990 | European Pat. Off. . |
| 0 417 866 A1 | 3/1991 | European Pat. Off. . |
| 2 196 376 | 3/1974 | France . |
| 33175 | 12/1964 | Germany . |
| 1916360 | 10/1970 | Germany . |
| 37 07 226 A1 | 9/1988 | Germany . |
| 38 03 899 C1 | 4/1989 | Germany . |
| 39 38 373 A1 | 5/1990 | Germany . |
| 0 466 958 | 1/1992 | Germany . |
| 1031764 | 6/1966 | United Kingdom . |
| 1 371 218 | 10/1974 | United Kingdom . |
| 1 371 219 | 10/1974 | United Kingdom . |
| 2 056 995 | 3/1981 | United Kingdom . |
| 1 592 802 | 7/1981 | United Kingdom . |

*Primary Examiner*—Helene Klemanski
*Attorney, Agent, or Firm*—Pillsbury Madison & Sutro LLP

[57] ABSTRACT

Surface-modified, pyrogenically produced mixed oxides which contain two or more components of the series $SiO_2$, $Al_2O_3$, $TiO_2$, $ZrO_2$, $Fe_2O_3$, $Nb_2O_5$, $V_2O_5$, $WO_3$, $SnO_2$, $GeO_2$ and have been surface-modified with one to several compounds of the following groups:

(a) organosilanes of the type $(RO)_3Si(C_nH_{2n+1})$,
(b) $R'_x(RO)_ySi(C_nH_{2n+1})$,
(c) $X_3Si(C_nH_{2n+1})$,
(d) $X_2(R')Si(C_nH_{2n+1})$,
(e) $X(R')_2Si(C_nH_{2n+1})$,
(f) $(RO)_3Si(CH_2)_m$—R',
(g) $(R'')_x(RO)_ySi(CH_2)_m$—R',
(h) $X_3Si(CH_2)_m$—R',
(i) $(R)X_2Si(CH_2)_m$—R',
(j) $(R)_2X\ Si(CH_2)_m$—R',
(k) Silazanes of the type

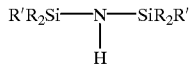

(l) Cyclic polysiloxanes,
(m) Polysiloxanes or silicone oils.

9 Claims, No Drawings

SURFACE-MODIFIED, PYROGENICALLY PRODUCED MIXED OXIDES, METHOD OF THEIR PRODUCTION AND USE

FIELD OF THE INVENTION

The invention relates to surface-modified, pyrogenically produced mixed oxides and methods of their production and use.

BACKGROUND INFORMATION

SUMMARY OF THE INVENTION

Subject matter of the invention constitutes surface-modified, pyrogenically produced mixed oxides which contain two or more components of the series $SiO_2$, $Al_2O_3$, $TiO_2$, $ZrO_2$, $Fe_2O_3$, $Nb_2O_5$, $V_2O_5$, $WO_3$, $SnO_2$, $GeO_2$ and were surface-modified with one or several compounds of the following groups:

(a) Organosilanes of the type $(RO)_3Si(C_nH_{2n+1})$
  R=alkyl, such as e.g. methyl-, ethyl-, n-propyl-, i-propyl-, butyl—
  n=1–20

(b) Organosilanes of the type $R'_x(RO)_ySi(C_nH_{2n+1})$
  R=alkyl, such as e.g. methyl-, ethyl-, n-propyl-, i-propyl-, butyl—
  R=alkyl such as e.g. methyl-, ethyl-, n-propyl-, i-propyl-, butyl—
  n=1–20
  x=y=3
  x=1, 2
  y=1, 2

(c) Halogenorganosilanes of the type $X_3Si(C_nH_{2n+1})$
  X=Cl, Br
  n=1–20

(d) Halogenorganosilanes of the type $X_2(R')Si(C_nH_{2n+1})$
  X=Cl, Br
  R'=alkyl, such as e.g. methyl-, ethyl-, n-propyl-, i-propyl-, butyl—
  n=1–20

(e) Halogenorganosilanes of the type $X(R')_2Si(C_nH_{2n+1})$
  X=Cl, Br
  R'=alkyl, such as e.g. methyl-, ethyl-, n-propyl-, i-propyl-, butyl—
  n=1–20

(f) Organosilanes of the type $(RO)_3Si(CH_2)_m—R'$
  R=alkyl, such as methyl-, ethyl-, propyl—
  m=0, 1–20
  R'=methyl-, aryl (e.g. $—C_6H_5$, substituted phenyl groups)
  $—C_4F_9$, $OCF_2—CHF—CF_3$, $—C_6F_{13}$, $—O—CF_2—CHF_2$
  $—NH_2$, $—N_3$, $—SCN$, $—CH=CH_2$,
  $—OOC(CH_3)C=CH_2$
  $—OCH_2—CH(O)CH_2$

$—NH—COO—CH_3$, $—NH—COO—CH_2—CH_3$,
$—NH—(CH_2)_3Si(OR)_3$
$—S_x—(CH_2)_3Si(OR)_3$ (g) Organosilanes of the type $(R'')_x(RO)_ySi(CH_2)_m—R'$
  $R''$ = alkyl  $x + y = 3$
  $x = 1, 2$
  $y = 1, 2$
  $m = 0, 1$ to $20$ R'=methyl-, aryl (e.g. $—C_6H_5$, substituted phenyl groups)
$—C_4F_9$, $OCF_2—CHF—CF_3$, $—C_6F_{13}$, $—O—CF_2—CHF_2$
$—NH_2$, $—N_3$, $—SCN$, $—CH=CH_2$,
$—OOC(CH_3)C=CH_2$
$—OCH_2—CH(O)CH_2$

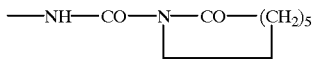

$—NH—COO—CH_3$, $—NH—COO—CH_2—CH_3$,
$—NH—(CH_2)_3Si(OR)_3$
$—S_x—(CH_2)_3Si(OR)_3$ (h) Halogenorganosilanes of the type $X_3Si(CH_2)_m—R'$
  X=Cl, Br
  m=0, 1–20
  R'=methyl-, aryl (e.g. $—C_6H_5$, substituted phenyl groups)
  $—C_4F_9$  $OCF_2—CHF—CF_3$, $—C_6F_{13}$, $—O—CF_2—CHF_2$
  $—NH_2$, $—N_3$, $—SCN$, $—CH=CH_2$,
  $—OOC(CH_3)C=CH_2$
  $—OCH_2—CH(O)CH_2$

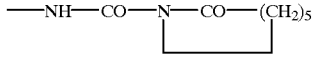

$—NH—COO—CH_3$, $—NH—COO—CH_2—CH_3$,
$—NH—(CH_2)_3Si(OR)_3$
$—S_x—(CH_2)_3Si(OR)_3$ (i) Halogenorganosilanes of the type $(R)X_2Si(CH_2)_m—R'$
  X=Cl, Br
  R=alkyl, such as methyl-, ethyl-, propyl—
  m=0, 1–20
  R'=methyl-, aryl (e.g. $—C_6H_5$, substituted phenyl groups)
  $—C_4F_9$, $OCF_2—CHF—CF_3$, $—C_6F_{13}$, $—O—CF_2—CHF_2$
  $—NH_2$, $—N_3$, $—SCN$, $—CH=CH_2$,
  $—OOC(CH_3)C=CH_2$
  $—OCH_2—CH(O)CH_2$

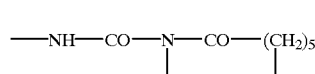

$—NH—COO—CH_3$, $—NH—COO—CH_2—CH_3$,
$—NH—(CH_2)_3Si(OR)_3$,
$—S_x—(CH_2)_3Si(OR)_3$ (j) Halogenorganosilanes of the type $(R)_2X Si(CH_2)_m—R'$
  X=Cl, Br
  R=alkyl m=0, 1–20
R'=methyl-, aryl (e.g. —$C_6H_5$, substituted phenyl groups)
—$C_4F_9$, $OCF_2$—CHF—$CF_3$, —$C_6F_{13}$, —O—$CF_2$—$CHF_2$
—$NH_2$, —$N_3$, —SCN, —CH=$CH_2$,
—$OOC(CH_3)C$=$CH_2$
—$OCH_2$—$CH(O)CH_2$

—NH—CO—N—CO—$(CH_2)_5$

—NH—COO—$CH_3$, —NH—COO—$CH_2$—$CH_3$,
—NH—$(CH_2)_3Si(OR)_3$
—$S_x$—$(CH_2)_3Si(OR)_3$ (k) Silazanes of the type $R'R_2Si$—N—$SiR_2R'$
         |
         H R=alkyl
R'=alkyl, vinyl (l) Cyclic polysiloxanes of the type D 3, D 4, D 5 in which D 3, D 4 and D 5 signify cyclic polysiloxanes with 3, 4 or 5 units of the type —O—$Si(CH_3)_2$—, e.g. octamethylcyclotetrasiloxane=D 4

[Structure of octamethylcyclotetrasiloxane]

(m) polysiloxanes or silicone oils of the type

[Structure of polysiloxane with Y—O—[[Si(R)(R')—O]_m[Si(R'')(R''')—O]_n]_u—Y]

$m = 0, 1, 2, 3, ... \infty$
$n = 0, 1, 2, 3, ... \infty$
$u = 0, 1, 2, 3, ... \infty$
Y = $CH_3$, H, $C_nH_{2n+1}$   n = 1–20
Y = $Si(CH_3)_3$, $Si(CH_3)_2H$
    $Si(CH_3)_2OH$, $Si(CH_3)_2(OCH_3)$
    $Si(CH_3)_2(C_nH_{2n+1})$   n = 1–20

R=alkyl such as $C_nH_{2n+1}$ in which n=1 to 20, aryl such as phenyl- and substituted phenyl groups, $(CH_2)_n$—$NH_2$, H R'=alkyl such as $C_nH_{2n+1}$ in which n=1 to 20, aryl such as phenyl- and substituted phenyl groups, $(CH_2)_n$—$NH_2$, H R''=alkyl such as $C_nH_{2n+1}$ in which n=1 to 20, aryl such as phenyl- and substituted phenyl groups, $(CH_2)_n$—$NH_2$, H R'''=alkyl such as $C_nH_{2n+1}$ in which n=1 to 20, aryl such as phenyl- and substituted phenyl groups, $(CH_2)_n$—$NH_2$, H Further subject matter of the invention is constituted by a method of producing the surface-modified, pyrogenically produced mixed oxides in accordance with the invention which is characterized in that two or more metal chlorides of the series $SiCl_4$, $AlCl_3$, $TiCl_4$, $ZrCl_4$, $FeCl_3$, $NbCl_5$, $VOCl_3$, $WOCl_4$, $WCl_6$, $SnCl_4$ and $GeCl_4$ are evaporated [vaporized] together or separately, transferred together with an inert gas, e.g. nitrogen, into the mixing chamber of a known burner, mixed there with hydrogen, air and/or oxygen, the multi-component mixture burned in a reaction chamber, the solid mixed oxides separated thereafter from the gaseous reaction products and optionally freed in moist air from adhering hydrogen chloride and the pyrogenically produced mixed oxides placed in a suitable mixing container, the mixed oxides sprayed under intensive mixing optionally with water at first and then with the surface-modifying reagent or the mixture of several surface-modifying reagents, mixed again 15 to 30 minutes and subsequently tempered at a temperature of 100 to 400° C. for a period of 1 to 6 hours.

The water used can be acidified with an acid, e.g. hydrochloric acid, from pH 7 to 1. The surface-modifying reagent used can be dissolved in a suitable solvent such as e.g. ethanol. The mixing and/or tempering can be carried out in an atmosphere of protective gas such as, for example, nitrogen.

Further subject matter of the invention constitutes a method of producing the surface-modified, pyrogenically produced mixed oxides which is characterized in that two or more metal chlorides from the series $SiCl_4$, $AlCl_3$, $TiCl_4$, $ZrCl_4$, $FeCl_3$, $NbCl_5$, $VOCl_3$, $WOCl_4$, $WCl_6$, $SnCl_4$ and $GeCl_4$ are evaporated [vaporized] together or separately, transferred together with an inert gas, e.g. nitrogen, into the mixing chamber of a known burner, mixed there with hydrogen, air and/or oxygen. The multi-component mixture is burned in a reaction chamber, the solid mixed oxides separated thereafter from the gaseous reaction products and optionally freed in moist air from adhering hydrogen chloride and mixed as homogeneously as possible with organohalogen silanes with the exclusion of oxygen, the mixture heated together with slight amounts of water vapor and optionally together with an inert gas in a continuous process [continuous-current process which takes place in a continuous manner] in an upright treatment space designed as a tubular oven to temperatures of 200 to 800° C., preferably 400 to 600° C., the solid and gaseous reaction products separated from each other and the solid products optionally deacidified and dried.

Further subject matter of the invention constitutes the use of the surface-modified, pyrogenically produced mixed oxides in accordance with the invention as Reinforcement filler in silicone rubber and gum,
Charge stabilizer and flow aid in toner powder,
Free-flow agent,
Anti-blocking aid, e.g. in foils,
UV blocker, e.g. in cosmetics,
Thickening agent, e.g. in paints.

DETAILED DESCRIPTION OF THE INVENTION

Examples
Examples for the Production of Mixed Oxides

Metal chlorides 1 and 2 are volatilized in separate evaporators and the chloride vapors conducted by means of nitrogen into the mixing chamber of a burner. There they are mixed with hydrogen and dried air and/or oxygen and burned in a reaction chamber. The reaction products are cooled down to approximately 110° C. in the coagulation zone and the mixed oxides produced are subsequently separated off with a filter. Adhering chloride is removed by treating the powders with moist air at temperatures between 500 and 700° C.

The reaction conditions and the product qualities for the various mixed oxides are collated in table 1.

Examples for the Production of Surface-Modified Mixed Oxides

The reaction conditions and stoichiometric ratios for the surface modification are shown in table 2. The physico-chemical data are collated in table 3.

TABLE 1

Reaction conditions and product qualities of a few mixed oxides

| Mixed oxide example | Oxide 1 (wt. %) | Oxide 2 (wt. %) | Metal chloride 1 (g/h) | Metal chloride 2 (g/h) | $H_2$ (l/h) | Air (l/h) | BET ($m^2/g$) | Tapped density (g/l) | Loss on ignition (%) | Chloride content (%) |
|---|---|---|---|---|---|---|---|---|---|---|
| 1 | $SiO_2$ 7.5 | $TiO_2$ 92.5 | $SiCl_4$ 50 | $TiCl_4$ 516 | 470 | 3280 | 95 | 85 | 0.6 | 0.1 |
| 2 | $Al_2O_3$ 15 | $SiO_2$ 85 | $AlCl_3$ 126 | $SiCl_4$ 778 | 300 | 1300 | 179 | 104 | 2.9 | 0.12 |
| 3 | $Fe_2O_3$ 2 | $TiO_2$ 98 | $FeCl_3$ 29 | $TiCl_4$ 1697 | 525 | 3079 | 53 | 175 | 1.2 | 0.3 |
| 4 | $Fe_2O_3$ 7 | $TiO_2$ 93 | $FeCl_3$ 107 | $TiCl_4$ 1613 | 525 | 3079 | 46 | 185 | 1.7 | 0.4 |
| 5 | $SiO_2$ 87 | $ZrO_2$ 13 | $SiCl_4$ 1303 | $ZrCl_4$ 135 | 800 | 2420 | 121 | 48 | 0.9 | 0.24 |
| 6 | $Al_2O_3$ 11 | $TiO_2$ 89 | $AlCl_3$ 188 | $TiCl_4$ 793 | 448 | 1276 | 47 | 329 | 0.7 | 0.16 |
| 7 | $Al_2O_3$ 25 | $TiO_2$ 75 | $AlCl_3$ 464 | $TiCl_4$ 1269 | 525 | 3579 | 72 | 120 | 1.1 | 0.6 |
| 8 | $TiO_2$ 95 | $ZrO_2$ 5 | $TiCl_4$ 1661 | $ZrCl_4$ 78 | 525 | 3080 | 59 | 218 | 0.9 | 0.15 |

TABLE 2

| Example | Designation | Mixed oxide | Modifying reagent* | Modifying reagent (g/100 g mixed oxide) | Amount of water (g/100 g mixed oxide) | Amount of solvent (g/100 g mixed oxide) | Tempering time (h) | Tempering temperature (° C.) |
|---|---|---|---|---|---|---|---|---|
| 9 | VT 772 | 4 | 1 | 10 | 0 | 0 | 4 | 140 |
| 10 | VT 773 | 4 | 2 | 10 | 0 | 0 | 2 | 120 |
| 11 | VT 774 | 4 | 3 | 10 | 0 | 0 | 2.5 | 250 |
| 12 | VT 816 | 3 | 1 | 10 | 0 | 0 | 3 | 180 |
| 13 | VT 817 | 3 | 2 | 10 | 0 | 0 | 2 | 120 |
| 14 | VT 818 | 3 | 3 | 10 | 0 | 0 | 2.5 | 250 |
| 15 | VT 775 | 2 | 1 | 20 | 0 | 0 | 4 | 140 |
| 16 | VT 776 | 2 | 2 | 16 | 0 | 0 | 2 | 120 |
| 17 | VT 777 | 2 | 3 | 15 | 0 | 0 | 2 | 250 |
| 18 | VT 819 | 8 | 1 | 10 | 0 | 0 | 4 | 180 |
| 19 | VT 820 | 8 | 2 | 10 | 0 | 0 | 2 | 120 |
| 20 | VT 821 | 8 | 3 | 10 | 0 | 0 | 2.5 | 250 |
| 21 | VT 900 | 4 | 2 | 12 | 5 | 0 | 2.5 | 140 |
| 22 | VT 901 | 3 | 2 | 10 | 0 | 10** | 2.5 | 140 |
| 23 | VT 747 | 6 | 2 | 5 | 0 | 0 | 2 | 129 |
| 24 | VT 748 | 6 | 2 | 10 | 0 | 0 | 2 | 120 |
| 25 | VT 749 | 6 | 4 | 10 | 0 | 0 | 2 | 120 |
| 26 | VT 750 | 7 | 2 | 10 | 0 | 0 | 2 | 120 |
| 27 | VT 751 | 7 | 4 | 10 | 0 | 0 | 2 | 120 |
| 28 | VT 719 | 5 | 1 | 10 | 5 | 0 | 3 | 130 |
| 29 | VT 734 | 1 | 3 | 10 | 0 | 0 | 2 | 250 |

Footnotes to Table 2:
*1 = hexamethyldisilazane = $(CH_3)_3Si\text{—}NH\text{—}Si(CH_3)_3$
2 = trimethoxyoctylsilane = $(CH_3O)_3Si\text{—}(CH_2)_7\text{—}CH_3$

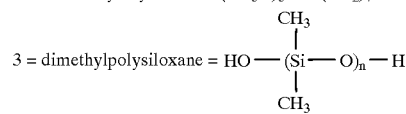

3 = dimethylpolysiloxane = $HO\text{—}(Si(CH_3)_2\text{—}O)_n\text{—}H$

4 = trimethoxypropylsilane = $(CH_3O)_3Si\text{—}CH_2\text{—}CH_2\text{—}CH_3$
** = ethanol

TABLE 3

| Example | Designation | Specific surface according to BET (m²/g) | Tapped density (g/l) | Drying loss (%) | Loss of ignition (%) | pH | Carbon content (%) |
|---|---|---|---|---|---|---|---|
| 9 | VT 772 | 40 | 269 | 0.0 | 1.3 | 6.4 | 0.5 |
| 10 | VT 773 | 36 | 280 | 0.1 | 4.7 | 3.4 | 3.6 |
| 11 | VT 774 | 27 | 301 | 0.2 | 3.9 | 3.4 | 2.7 |
| 12 | VT 816 | 45 | 258 | 0.4 | 1.1 | 7.5 | 0.5 |
| 13 | VT 817 | 39 | 288 | 0.7 | 3.9 | 3.4 | 3.5 |
| 14 | VT 818 | 32 | 292 | 0.0 | 3.6 | 3.6 | 2.9 |
| 15 | VT 775 | 124 | 127 | 0.5 | 3.4 | 6.6 | 1.7 |
| 16 | VT 776 | 111 | 136 | 1.0 | 9.5 | 4.2 | 5.8 |
| 17 | VT 777 | 101 | 136 | 0.9 | 4.7 | 4.2 | 2.9 |
| 18 | VT 819 | 51 | 245 | 0.5 | 0.7 | 9.0 | 0.4 |
| 19 | VT 820 | 45 | 275 | 0.0 | 4.4 | 4.0 | 3.6 |
| 20 | VT 821 | 35 | 275 | 0.0 | 2.3 | 4.1 | 2.5 |
| 21 | VT 900 | 34 | 275 | 0.1 | 4.9 | 3.5 | 3.9 |
| 22 | VT 901 | 38 | 282 | 0.6 | 4.0 | 3.6 | 3.6 |
| 23 | VT 747 | 31 | 396 | 0.2 | 1.7 | 3.7 | 2.0 |
| 24 | VT 748 | 23 | 409 | 0.3 | 4.8 | 4.0 | 3.9 |
| 25 | VT 749 | 26 | 402 | 0.3 | 2.3 | 4.1 | 1.8 |
| 26 | VT 750 | 56 | 161 | 0.3 | 16.8 | 3.8 | 3.9 |
| 27 | VT 751 | 55 | 162 | 0.2 | 2.7 | 4.1 | 2.0 |
| 28 | VT 719 | 60 | 60 | 0.1 | 1.1 | 6.4 | 1.3 |
| 29 | VT 734 | 74 | 114 | 0.5 | 2.5 | 4.2 | 2.5 |

What is claimed is:

1. Surface-modified, pyrogenically produced mixed oxides which contain two or more components from the series consisting of $SiO_2$, $Al_2O_3$, $TiO_2$, $ZrO_2$, $Fe_2O_3$, $Nb_2O_5$, $V_2O_5$, $WO_3$, $SnO_2$, and $GeO_2$ which have been freed from adhering hydrogen chloride in moist air and do not undergo a drying step prior to hydrophobing and were surface-modified with one or more compounds of the following groups:

(a) Organosilanes of the formula $(RO)_3Si(C_nH_{2n+1})$
R=alkyl
n=1–20

(b) Organosilanes of the formula $R'_x(RO)_ySi(C_nH_{2n+1})$
R=alkyl
R'=alkyl
n=1–20
x+y=3
x=1, 2
y=1, 2

(c) Halogenorganosilanes of the formula $X_3Si(C_nH_{2n+1})$
X=Cl, Br
n=1–20

(d) Halogenorganosilanes of the formula $X_2(R')Si(C_nH_{2n+1})$
X=Cl, Br
R'=alkyl
n=1–20

(e) Halogenorganosilanes of the formula $X(R')_2Si(C_nH_{2n+1})$
X=Cl, Br
R'=alkyl
n=1–20

(f) Organosilanes of the formula $(RO)_3Si(CH_2)_m$—R'
R=alkyl
m=0, 1–20
R'=methyl-, aryl
—$C_4F_9$, $OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$,
—$OCH_2$—CH(O)$CH_2$,

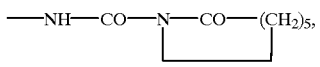

—NH—COO—$CH_3$, —NH—COO—$CH_2$—$CH_3$,
—NH—$(CH_2)_3$Si$(OR)_3$ (g) Organosilanes of the formula $(R'')_x(RO)_ySi(CH_2)_m$—R'

R″ = alkyl  x + y = 3 x = 1, 2 y = 1, 2 m = 0, 1 to 20

R'=methyl-, aryl
—$C_4F_9$, $OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$

—NH—COO—$CH_3$, —NH—COO—$CH_2$—$CH_3$,
—NH—$(CH_2)_3$Si$(OR)_3$ (h) Halogenorganosilanes of the formula $X_3Si(CH_2)_m$—R'
X=Cl, Br
m=0, 1–20
R'=methyl-, aryl
—$C_4F_9$, $OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$

—OCH$_2$—CH(O)CH$_2$

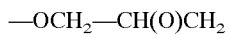

—NH—COO—CH$_3$, —NH—COO—CH$_2$—CH$_3$,
—NH—(CH$_2$)$_3$Si(OR)$_3$ (i) Halogenorganosilanes of the formula (R)X$_2$Si(CH$_2$)$_m$—R'
X=Cl, Br
R=alkyl
m=0, 1–20
R'=methyl-, aryl
—C$_4$F$_9$, OCF$_2$—CHF—CF$_3$, —C$_6$F$_{13}$, —O—CF$_2$—CHF$_2$
—NH$_2$, —N$_3$, —SCN, —CH=CH$_2$,
—OOC(CH$_3$)C=CH$_2$
—OCH$_2$—CH(O)CH$_2$

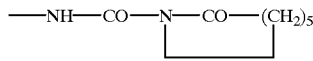

—NH—COO—CH$_3$, —NH—COO—CH$_2$—CH$_3$,
—NH—(CH$_2$)$_3$Si(OR)$_3$ (j) Halogenorganosilanes of the formula (R)$_2$X Si(CH$_2$)$_m$—R'
X=Cl, Br
R=alkyl
m=0, 1–20
R'=methyl-, aryl
—C$_4$F$_9$, OCF$_2$—CHF—CF$_3$, —C$_6$F$_{13}$, —O—CF$_2$—CHF$_2$
—NH$_2$, —N$_3$, —SCN, —CH=CH$_2$,
—OOC(CH$_3$)C=CH$_2$
—OCH$_2$—CH(O)CH$_2$

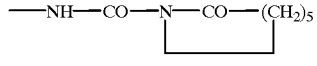

—NH—COO—CH$_3$, —NH—COO—CH$_2$—CH$_3$,
—NH—(CH$_2$)$_3$Si(OR)$_3$ (k) Silazanes of the formula

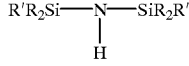

R=alkyl
R'=alkyl, vinyl (l) Cyclic polysiloxanes of the formula D 3, D 4, D 5,

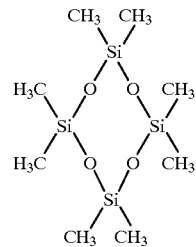

(m) polysiloxanes or silicone oils of the formula

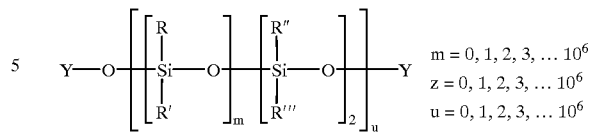

$m = 0, 1, 2, 3, \ldots 10^6$
$z = 0, 1, 2, 3, \ldots 10^6$
$u = 0, 1, 2, 3, \ldots 10^6$ Y = CH$_3$, H, C$_n$H$_{2n+1}$ n = 1-20
Y = Si(CH$_3$)$_3$, Si(CH$_3$)$_2$H
Si(CH$_3$)$_2$OH, Si(CH$_3$)$_2$(OCH$_3$)
Si(CH$_3$)$_2$(C$_n$H$_{2n+1}$) n = 1-20

R=alkyl, aryl, (CH$_2$)$_n$—NH$_2$, H
R'=alkyl, aryl, (CH$_2$)$_n$—NH$_2$, H
R"=alkyl, aryl, (CH$_2$)$_n$—NH$_2$, H
R'''=alkyl, aryl, (CH$_2$)$_n$—NH$_2$, H, wherein n=1–20.

2. Surface-modified, pyrogenically produced mixed oxides according to claim 1 which have been sprayed with additional water prior to hydrophobing.

3. A process for the preparation of surface-modified, pyrogenically produced mixed oxides according to claim 1, wherein two or more metal chlorides selected from the group consisting of SiCl$_4$, AlCl$_3$, TiCl$_4$, ZrCl$_4$, FeCl$_{31}$, NbCl$_5$, VOCl, WoCl$_4$, WCl$_6$, SnCl$_4$, and GeCl$_4$ are evaporated together or separately, transferred together with an inert gas into the mixing chamber of a known burner, mixed there with hydrogen, air and/or oxygen, the multi-component mixture is burned in a reaction chamber, the solid mixed oxides are then separated from the gaseous reaction products and freed from adhering hydrogen chloride in moist air, and the progenically produced mixed oxides are charged to a suitable mixing vessel, the mixed oxides are aprayed, with intensive mixing, and subsequently with the surface-modifying reagen or the mixture of several surface-modifying reagents, mixed agin for 15 to 30 minutes and subsequently heat-treated at a temperature of 100 to 400° C. for a period of 1–6 hours.

4. A process for the preparation of surface-modified, pyrogenically produced mixed oxides according to claim 1, wherein two or more metal chlorides selected from the group consisting of SiCl$_4$, AlCl$_3$, TiCl$_4$, ZrCl$_4$, FeCl$_3$, NbCl$_5$, VOCl, WoCl$_4$, WCl$_6$, SnCl$_4$, and GeCl$_4$ are evaporated together or separately, transferred together with an inert gas into the mixing chamber of a known burner, mixed there with hydrogen, air and/or oxygen, the multi-component mixture is burned in a reaction chamber, the solid mixed oxides are then separated from the gaseous reaction products and freed from adhering hydrogen chloride in moist air, and mixed as homogeneously as possible with organohalogen silanes with the exclusion of oxygen, and the mixture together with small quantities of water vapor and optionally together with an inert gas is heated to temperatures from 200 to 800° C., in the continuous co-current process in a treatment chamber having the form of an upright tubular furnace, the solid and gaseous reaction products are separated from each other, and the solid products are deacidified and dried.

5. The process of claim 4 wherein the temperature is 400 to 600° C.

6. The process according to claim 3 which further comprises the step of spraying with additional water prior to hydrophobing.

7. The process according to claim 4 which further comprises the step of spraying with additional water prior to hydrophobing.

8. The process according to claim 5 which further comprises the step of spraying with additional water prior to hydrophobing.

9. A surface-modified, pyrogenically produced mixed oxide according to claim 1 in the form of a reinforcing filler in silicone rubber or rubber, a charge stabilizer or free-flow agent in a toner powder, a free-flow agent, an anti-blocking agent, a UV blocker, or a thickener.

* * * * *